United States Patent [19]

Modolell et al.

[11] 4,142,940
[45] Mar. 6, 1979

[54] CULTIVATION CONTAINERS FOR CULTURES, MICROORGANISMS, CELLS, TISSUE AND THE LIKE

[75] Inventors: Manuel Modolell, Fürstetten; Paul G. Munder, Emmendingen; Herbert Schaus, Hanau am Main, all of Fed. Rep. of Germany

[73] Assignee: W. C. Heraeus GmbH, Hanau, Fed. Rep. of Germany

[21] Appl. No.: 720,993

[22] Filed: Sep. 7, 1976

[30] Foreign Application Priority Data

Sep. 13, 1975 [DE] Fed. Rep. of Germany ....... 2541000

[51] Int. Cl.² .............................................. C12K 1/10
[52] U.S. Cl. .................................. 195/139; 215/247; 215/261; 215/364; 220/89 A; 220/258
[58] Field of Search ................ 195/139, 127; 215/247, 215/261, 364; 220/89 A, 258

[56] References Cited

U.S. PATENT DOCUMENTS 3,760,969  9/1973  Shimamoto et al. ................. 215/247
3,932,222  1/1976  Dorn ................................... 195/127

Primary Examiner—Raymond N. Jones
Assistant Examiner—Robert J. Warden
Attorney, Agent, or Firm—Flynn & Frishauf

[57] ABSTRACT

To provide a disposable container which can be prefabricated under sterile conditions, a pair of concentric plastic rings are formed with interfitting, interlocking projection and recess means permitting the rings to be snapped together, the rings being additionally formed with matching fitting surfaces to interpose the edge portion of a gas permeable membrane therebetween so that, when the membrane is placed on the outer ring and the two rings are snapped together, the membrane is irremovably held. Preferably, the outer ring is made of a softer, yielding plastic, the inner ring of a more rigid plastic, with a projection snapping into a groove formed on the inner, more rigid ring, and the matching clamping surfaces for the membrane forming a sinuous, tortuous path with a flexible projecting lip on the outer ring fitting into a recess to clamp the membrane and seal the membrane in the structure.

10 Claims, 1 Drawing Figure

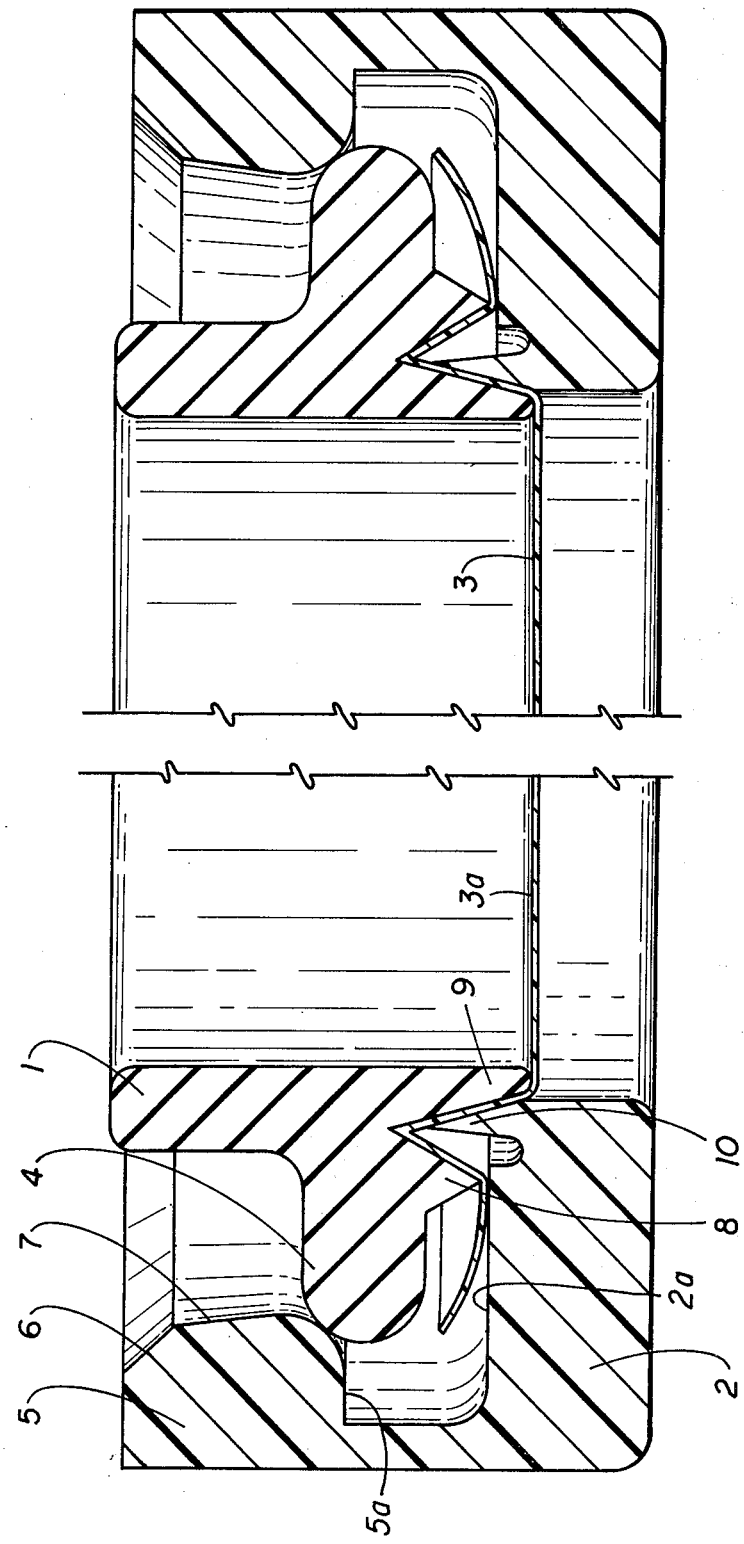

CULTIVATION CONTAINERS FOR CULTURES, MICROORGANISMS, CELLS, TISSUE AND THE LIKE

The present invention relates to a cultivation container or vessel, and more particularly to a cultivation container for cultures, microorganisms, cells, tissue and the like, and which uses a stretched gas permeable plastic membrane or foil as the bottom thereof, the membrane being clamped at the edge portion in a clamping holder.

Cultivation vessels of this type have previously been proposed. Generally, they include a ring shaped base plate which is formed with a groove in which a ring shaped cover plate with a comb-like projection fits; the gas permeable plastic foil is engaged between the cover plate and the ring shaped base plate. An additional plastic ring is provided to form the wall of the container or vessel. The gas permeable but impermeable to liquid plastic foil or membrane forms the bottom of the vessel and it is clamped by interlocking of the projection of the cover plate in the groove of the base plate. The clamping and stretching of the plastic foil is effected by pressure screws, threads, or the like.

It has also been proposed to provide cultivation vessels in the form of bags made of gas permeable plastic to cultivate tissue and the like. The inner surface of the plastic bag is roughened in order to favor growth of cells thereon. The kind of plastic useful in accordance with the invention to cultivate tissue and the like is described in U.S. Pat. No. 3,941,662.

The cultivation devices previously proposed to cultivate microorganisms previously were made or assembled just before the microorganisms were ready to be cultivated. This required substantial time, particularly of research personnel, which, however, was considered necessary in view of the importance of the use of the grown microorganisms.

It is an object of the present invention to provide a cultivating vessel which can be manufactured as a ready product, which is inexpensive, and in which the cost and the equipment necessary for reuse, sterilization, and reassembly can be avoided.

SUBJECT MATTER OF THE PRESENT INVENTION

Briefly, a clamping arrangement is made of two concentrically arranged rings made of plastic, the rings being formed with corresponding projections and recesses to lock them together. The rings, further, are formed with clamping surfaces to clamp the plastic membrane therebetween. Preferably, the plastic membrane is roughened at least on one side thereof.

The invention will be described by way of example with reference to the accompanying drawing, wherein:

The single FIGURE is a schematic cross-sectional view through the vessel or container of the present invention.

An inner plastic ring 1 is surrounded by an outer plastic ring 2. The bottom of the vessel is formed by a gas permeable plastic foil membrane 3. The inner plastic ring 1 is formed with a projecting ridge or bead 4 at its outer circumference, which fits beneath a projection 5 at the inner surface of the outer ring 2. The projection 5 forms the limiting part of a groove 5a in the outer ring 5. The projection 5 merges actually outwardly in a conical surface 7 which merges into a more shallow conical surface 6, forming a centering cone for assembly of the inner ring 1 into outer ring 2. The bottom of the inner ring 1 is formed with a sealing lip 8 which is shaped to terminate in a knife edge. The inner ring 1 is, additionally, formed with an abutment projection 9 to guide the edge portion of the plastic foil. The projection 9 defines in its outer side a groove in which a projecting lip 10 from the outer ring 2 can engage. The foil membrane 3 is clamped between the lip 10 and the abutment projection 9 in self-holding relation. The additional sealing lip 8 bearing against sealing surface 2a on outer ring 2 provides for further sealing of the parts and also defines the limiting engagement position of rings 1 and 2.

The rings 1, 2, are made of different plastic, as indicated by the different shadings in the FIGURE. The inner ring 1 is formed of a hard, essentially rigid plastic; the outer ring 2 is formed of a softer, and more flexible plastic. This arrangement is preferred, although the relationship of rigid and flexible plastic with respect to the rings can be reversed, just as the projections 4, 5 locking against each other can be reversed. The more flexible, softer plastic is, preferably, polyvinyl chloride, polypropylene, or high density, or high pressure polyethylene; the hard plastic is preferably polystyrol, or a polycarbonate. The vessel, preferably, is cup shaped and can be furnished with a removable cover, preferably made of transparent plastic.

The sealing lip 8 is not strictly necessary, although desirable. The projection 4 fits into the groove defined by the projection 5 of the outer ring 2 and, once assembled, is held irremovably therein. The inner sealing lip 10 fitting against a groove defined by the abutment projection 9 of the inner ring is preferably flexible, which is inherently given by making the projection 10 of smaller cross sectional diameter and, in accordance with the preferred embodiment, forming the outer ring 2 of the yielding more softer plastic, so that the membrane 3 will be securely held by the abutment projection 9 and the lip 10, the lip 10 being slightly deflected upon assembly of the parts together.

The arrangement permits assembling the membrane 3 to be free of wrinkles, folds, or undulations and to be tightly stretched, providing a liquid tight clamping thereof and holding liquid reliably for long periods of time. The simple form of the plastic rings permits inexpensive manufacture, and additionally automated assembly together with the gas permeable plastic foil under sterile conditions. The plastic foil, preferably, is roughened at least at the upper surface 3a (with reference to the FIGURE). Mistakes or misassembly upon assembling the cultivation vessels in the field are thus excluded. The structure lends itself to inexpensive and automated manufacture and assembly and thus permits production of the vessel as a disposable article. This is particularly important when used under clinical conditions. The selection of the plastic materials so that one of the rings is made of a harder plastic than the other provides an excellent seal between the parts and further facilitates assembly of the rings into each other.

Various change and modifications may be made, and, particularly, the relative relationships of the interlock projections and grooves can be reversed. Forming the inner ring 1 as the rigid, hard plastic has the advantage that the foil 3 is always reliably stretched.

Stretching the membrane between the inner projection 9 of the inner ring and the projection 10 of the outer ring forming the interengaging fitting surfaces can be carried out under sterile conditions, resulting in a container which is inexpensive and lends itself to reassembly, or for disposable use. The arrangement permits assembling the membrane to be tightly stretched, providing a liquid tight clamping thereof and holding liquids reliably for long periods of time.

We claim:

1. A cultivation container for cultures, microorganisms, cells, tissue, having a stretched, gas permeable, but impermeable to liquid membrane (3) forming the bottom thereof, and holding means to hold the membrane in position and in stretched and liquid tight condition comprising two concentric plastic rings (1,2) fitted in each other and having matching fitting surfaces (9,10) and interengaging and interlocking recess-projection locking means (4,5), the edge portion of the plastic membrane (3) being clamped between the adjacent matching fitting surfaces (9,10) in self-holding relation to lock and pinch the membrane in position between said matching, fitting surfaces when the rings are locked to each other and interlocking by engagement of the recess-projection locking means (4,5).

2. A container according to claim 1, wherein at least one of the plastic rings (1) is formed with a projecting sealing projection (3) and the other ring (2) is formed with a sealing surface (2a) facing said sealing projection (8), the membrane (3) being clamped between said sealing projection (8) and said sealing surface (2a).

3. A container according to claim 2, wherein the sealing projection (8) terminates in a knife edge.

4. A container according to claim 1, wherein the interengaging and interlocking recesses and projection means comprises a first bead (4) formed on one of the rings (1) at the surface facing the other ring, a second bead (5) defining a groove (5a) therebehind formed in the other ring (2) in the surface forming said first ring (1) to permit snapping the rings (12) together.

5. A container according to claim 1, wherein the interengaging and interlocking recess and projection means comprises a bead (4) formed at the surface of the inner ring (1) facing the outer ring (2), a projection (5) formed on the surface of the outer ring (2) facing the inner ring (1) and defining a groove (5a) therebehind;

and wherein the matching fitting surfaces comprise an inner locating projection (9) formed on the inner ring (1) and defining a groove therebehind, and an outer locating projection (10) formed on the outer ring (2) and engaging in the groove behind the inner locating projection.

6. A container according to claim 5, wherein the outer ring (2) is made of yielding, soft plastic, and the projecting lip (10) fitting behind the locating projection (9) of the inner ring is shaped and dimensioned to yieldingly deflect and clamp the membrane between the locating projection (9) and said lip.

7. A container according to claim 6, wherein the inner ring (1) is formed with a sealing projection (8), and the outer ring (2) has a surface (2a) facing a said sealing projection (8) to clamp the membrane between the sealing projection (8) and said surface (2a), said surface additionally, forming a locating stop for the inner ring to hold the bead (4) and the projection (5) in snapped-together, locked engagement, and the membrane (3) stretched between the inner locating projection (9) of the inner ring.

8. A container according to claim 1, wherein said rings (1,2) are made of different plastic materials, one of the rings being made of hard essentially rigid plastic and the other ring being made of plastic which is softer, and yielding with respect to the plastic of the first ring.

9. A container according to claim 1, wherein the inner ring (1) is made of essentially rigid, hard plastic and the outer ring is made of yielding and soft plastic.

10. A container according to claim 1, wherein the matching fitting surfaces comprise an inner locating projection (9) formed on the inner ring (1) and defining a groove therebehind, and an outer locating projection (10) formed on the outer ring (2) and engaging in the groove behind the inner locating projection, the membrane being stretched between the inner and outer locating projection (9) of the inner ring and being clamped in self locking relation between said inner and outer projection forming the matching, fitting surfaces.

* * * * *

UNITED STATES PATENT AND TRADEMARK OFFICE
CERTIFICATE OF CORRECTION

PATENT NO. : 4,142,940
DATED : March 6, 1979
INVENTOR(S) : Manuel MODOLELL

It is certified that error appears in the above-identified patent and that said Letters Patent are hereby corrected as shown below:

Claim 2, column 3, line 27, "projection (3)" should read -- projection (8) --

Claim 6, column 4, line 11 change "projecting lip" to -- outer locating projection -- line 11, before "locating" insert -- inner -- line 14, change "locating projection (9)" to -- inner and outer locating projections (9, 10) --

Signed and Sealed this

Twenty-fourth Day of July 1979

[SEAL]

Attest:

Attesting Officer

LUTRELLE F. PARKER
Acting Commissioner of Patents and Trademarks